United States Patent [19]

Hassall et al.

[11] Patent Number: 4,487,929
[45] Date of Patent: Dec. 11, 1984

[54] INTERMEDIATES FOR PYRAZOLOPYRIDAZINE DERIVATIVES

[75] Inventors: Cedric H. Hassall, Harpenden; Geoffrey Lawton, Hitchin; Christopher J. Moody, Stevenage, all of England

[73] Assignee: Hoffmann-La Roche, Inc., Nutley, N.J.

[21] Appl. No.: 488,508

[22] Filed: Apr. 25, 1983

Related U.S. Application Data

[62] Division of Ser. No. 272,351, Jun. 10, 1981, Pat. No. 4,399,136.

[30] Foreign Application Priority Data

Jun. 13, 1980 [GB] United Kingdom ............... 8019342
Mar. 11, 1981 [GB] United Kingdom ............... 8107621

[51] Int. Cl.³ .......................................... C07D 237/04
[52] U.S. Cl. .................................................. 544/224
[58] Field of Search ........................................ 544/224

[56] References Cited

U.S. PATENT DOCUMENTS 4,307,094 12/1981 Hassall et al. ...................... 424/250
4,341,781 7/1982 Hassall et al. ...................... 544/224

OTHER PUBLICATIONS

Molnar et al, Pharma. Acta. Helvetica, vol. 39 (1964) pp. 155–161.
Derwent Abstract No. 17676D for European Pat. No. 24,309.
Derwent Abstract No. 25836D for European Pat. No. 25,941.

Primary Examiner—Paul M. Coughlan, Jr.
Assistant Examiner—William A. Teoli, Jr.
Attorney, Agent, or Firm—Jon S. Saxe; Bernard S. Leon; William G. Isgro

[57] ABSTRACT

Intermediates of the formula

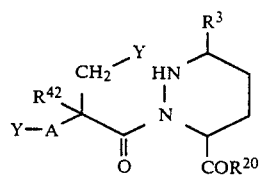

wherein A is methylene, ethylene or propylene which may be substituted by lower alkyl, Y is halogen, $R^3$ is hydrogen, lower alkyl, aryl or aryl-(lower alkyl)—, $R^{20}$ is lower alkoxy and $R^{42}$ is hydrogen, lower alkyl, aryl or aryl-(lower alkyl) or a group of the formula —A—Y in which A and Y are as above, are described.

1 Claim, No Drawings

INTERMEDIATES FOR PYRAZOLOPYRIDAZINE DERIVATIVES

This is a division, of application Ser. No. 272,351 filed June 10, 1981, now U.S. Pat. No. 4,399,136.

BRIEF SUMMARY OF THE INVENTION

The invention provides compounds of the formula

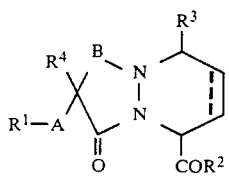

wherein A is methylene, ethylene or propylene which may be substituted by lower alkyl, B is carbonyl or methylene, $R^1$ is halogen, carboxyl, lower alkoxycarbonyl, hydroxyaminocarbonyl, mercapto, lower alkanoylthio or aryl-(lower alkylthio)-, $R^2$ is hydroxy, lower alkoxy or amino, $R^3$ is hydrogen, lower alkyl, aryl or aryl- (lower alkyl)—, $R^4$ is hydrogen, lower alkyl, aryl or aryl-(lower alkyl)—or a group of the formula —A—$R^1$, wherein A and $R^1$ are as described above and the broken line denotes an optional carbon-carbon bond which can be present only when B is carbonyl, or a salt of an acid formula I with pharmaceutically acceptable base. The compounds of formula I and their salts are useful as antihypertensive agents.

In another aspect, the invention relates to a process for the preparation of the compounds of formula I.

In still another aspect, the invention relates to intermediates hereinafter characterized by formula II,IV,V-,VI,VIII and IX.

In yet another aspect, the invention relates to pharmaceutical preparations or compositions containing a compound of formula I.

DETAILED DESCRIPTION OF THE INVENTION

The invention relates to pyrazolopyridazine derivatives. More particularly, the invention is concerned with pyrazolopyridazine derivatives, a process for their preparations, pharmaceutical preparations containing same and use thereof.

The pyrazolopyridazine derivatives of the invention are compounds of the formula

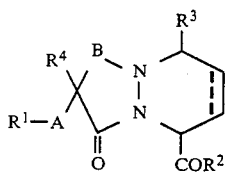

wherein A is methylene, ethylene or propylene which may be substituted by lower alkyl, B is carbonyl or methylene, $R^1$ is halogen, carboxyl, lower alkoxycarbonyl, hydroxyaminocarbonyl, mercapto, lower alkanoylthio or aryl(lower alkylthio)-group, $R^2$ is hydroxy, lower alkoxy or amino, $R^3$ is hydrogen, lower alkyl, aryl or aryl-(lower alkyl)-, $R^4$ is hydrogen, lower alkyl, aryl or aryl-(lower alkyl)—or a group of the formula —A—$R^1$ wherein A and $R^1$ are as described above and the broken line denotes an optional carbon-carbon bond which can be present only when B is carbonyl, or a salt of a compound of formula I, wherein $R^1$ is carboxy and/or $R^2$ is hydroxy, with a pharmaceutically acceptable base.

As used herein, the term "lower alkyl", alone or in combination, denotes a straight-chain or branched-chain alkyl group which preferably contains from 1 to 6 carbon atoms, for example, methyl, ethyl, propyl, isopropyl, butyl, tert.butyl, pentyl and hexyl. The term "lower alkoxy", alone or in combination, denotes a straight-chain or branched-chain alkoxy group which preferably contains from 1 to 6 carbon atoms, for example, methoxy, ethoxy, propoxy, isopropoxy and the like. Examples of lower alkoxycarbonyl groups are methoxyacarbonyl, ethoxycarbonyl and the like. The lower alkanoyl moiety of a lower alkanoylthio group is derived from a straight-chain or branched-chain alkanoic acid which preferably contains up to 6 carbons atoms such as acetic acid, propionic acid, butyric acid, isobutyric acid, valeric acid, pivalic acid and the like. Examples of lower alkanoylthio groups thus are acetylthio, propionylthio and the like. The term "aryl", alone or in combination, denotes a phenyl group or a phenyl group bearing one or more substituents selected from halogen, lower alkyl, lower alkoxy, trifluoromethyl and the like. An example of an aryl-(lower alkylthio) group is benzylthio group. The term "halogen" denotes fluorine, chlorine, bromine or iodine.

Preferred compounds of formula I are those wherein B is carbonyl. $R^1$ preferably is mercapto. $R^2$ preferably is hydroxy. The preferred meaning of $R^3$ is hydrogen. $R^4$ preferably is hydrogen or lower alkyl, particularly methyl or ethyl, or aryl-(lower alkyl), particularly benzyl. From the above, it follows that particularly preferred compounds of formula I are those wherein B is carbonyl, $R^1$ is mercapto, $R^2$ is hydroxy and $R^4$ is hydrogen, methyl, ethyl or benzyl.

An especially preferred compound of formula I hereinbefore is 2,3,5,8-tetrahydro-2-(2-mercaptoethyl)-2-methyl-1,3-dioxo-1H-pyrazolo[1,2a]pyridazone-5-carboxylic acid.

Further preferred compounds of formula I hereinbefore are:

Hexahydro 2-mercaptomethyl-2-methyl-1,3-dioxo-1H-pyrazolo[1,2-a]pyridazine-5-carboxylic acid, hexahydro 2-(2-mercaptoethyl)-2-methyl-1,3-dioxo-1H-pyrazolo[1,2-a]pyridazine-5-carboxylic acid, hexahydro 2-(2-mercaptoethyl)-1,3-dioxo-1H-pyrazolo[1,2-a]pyridazine-5-carboxylic acid;

hexahydro 2,2-bis(2-mercaptoethyl)-1,3-dioxo-1H-pyrazolo[1,2-a]pyridazine-5-carboxylic acid, 2 ethyl-hexahydro-2(2-mercaptoethyl)-1,3-dioxo-1H-pyrazolo[1,2-a]pyridazine-5-carboxylic acid;

2-benzyl-2,3,5,8-tetrahydro-2-(2-mercaptoethyl)-1,3-dioxo-1H-pyrazolo[1,2-a]pyridazine-5-carboxylic acid, 2-ethyl-2,3,5,8-tetrahydro-2-(2-mercaptoethyl)-1,3-dioxo-1H-pyrazolo[1,2-a]pyridazine-5-carboxylic acid, hexahydro-2-mercaptomethyl-3-oxo-1H-pyrazolo[1,2-a]-pyridazine-5-carboxylic acid and hexahydro-2-(2-mercaptoethyl)-2-methyl-3-oxo-1H-pyrazolo[1,2-a]pyridazine-5-carboxylic acid.

Other examples of interesting compounds of formula I are:

Diethyl 5-tert-butoxycarbonyl-hexahydro-1,3-dioxo-1H-pyrazolo[1,2-a]pyridazine-2,2-diacetate, 2,2-bis(2-ethoxycarbonylethyl)-hexahydro-1,3-dioxo-1H-pyrazolo[1,2-a]pyridazine-5-carboxylate,
tert-butyl 2,2bis(acetylthiomethyl)-hexahydro-1,3-dioxo-1H-pyrazolo[1,2-a]pyridazine-5-carboxylate,
tert-butyl-2,2-bis(2-acetylthioethyl)-hexahydro-1,3-dioxo-1H-pyrazolo[1,2-a]pyridazine-5-carboxylate,
tert-butyl 2-(2-acetylthioethyl)-hexahydro-1,3-dioxo-1H-pyrazolo[1,2-a]pyridazine-5-carboxylate,
tert.butyl 2acetylthiomethyl-hexahydro-2methyl-1,3-dioxo-1H-pyrazolo[1,2-a]pyridazine-5-carboxylate,
tert-butyl 2-(2-acetylthioethyl)-hexahydro-2methyl-1,3-dioxo-1H-pyrazolo[1,2-a]pyridazine-5-carboxylate;
tert.butyl 2-(3-acetylthiopropyl)-hexahydro-2-methyl-1,3-dioxo-1H-pyrazolo[1,2-a]pyridazine-5-carboxylate,
diethyl 5-carboxy-hexahydro-1,3-dioxo-1H-pyrazolo[1,2-a]pyridazine-2,2-diacetate,
5-carboxy-hexahydro-1,3-dioxo-1H-pyrazolo[1,2-a]-pyridazine-2,2-diacetic acid,
2(2acetylthioethyl)-hexahydro-2-methyl-1,3-dioxo-1H-pyrazolo[1,2-a]pyridazine-5-carboxylic acid,
2-(3-acetylthiopropyl)-hexahydro-2-methyl-1,3-dioxo-1H-pyrazolo[1,2-a]pyridazine-5-carboxylic acid,
methyl 2,3,5,8-tetrahydro-2-(2iodoethyl)-2-methyl-1,3-dioxo-1H-pyrazolo[1,2-a]pyridazine-5-carboxylate,
methyl 2-(2-acetylthioethyl)-2,3,5,8-tetrahydro-2-methyl-1,3-dioxo-1H-pyrazolo[1,2-a]pyridazine-5-carboxylate,
tert-butyl 2-(2-acetylthioethyl)-2-ethyl-hexahydro-1,3-dioxo-1H-pyrazolo[1,2-a]pyridazine-5-carboxylate,
2-(2-acetylthioethyl)-2-ethyl-hexahydro-1,3-dioxo-1H-pyrazolo[1,2-a]pyridazine-5-carboxylic acid,
methyl 2-benzyl-2,3,5,8-tetrahydro-2-(2-iodoethyl)-1,3-dioxo-1H-pyrazolo[1,2-a]pyridazine-5-carboxylate,
methyl 2-(2-acetylthioethyl)-2-benzyl-2,3,5,8-tetrahydro-1,3-dioxo-1H-pyrazolo[1,2-a]pyridazine-5-carboxylate,
methyl 2-ethyl-2,3,5,8-tetrahydro-2-(2-iodoethyl)-1,3-dioxo-1H-pyrazolo[1,2-a]pyridazine-5-carboxylate,
methyl 2-(2-acetylthioethyl)-2-ethyl-2,3,5,8-tetrahydro-1,3-dioxo-1H-pyrazolo[1,2-a]pyridazine-5-carboxylate,
tert.butyl hexahydro-2[(N-hydroxycarbamoyl)methyl]-2-methyl-1,3-dioxo-1H-pyrazolo[1,2]pyridazine-5-carboxylate,
hexahydro-2-[(N-hydroxycarbamoyl)methyl]-2-methyl-1,3-dioxo-1H-pyrazolo[1,2-a]pyridazine-5-carboxylic acid,
tert-butyl 2-bromomethyl-hexahydro-3-oxo-1H-pyrazolo[1,2-a]pyridazine-5-carboxylate,
tert.butyl 2-acetylthiomethyl-hexahydro-3-oxo-1H-pyrazolo[1,2-a]pyridazine-5-carboxylate,
2-acetylthiomethyl-hexahydro-3-oxo-1H-pyrazolo[1,2-a]-pyridazine-5-carboxylic acid and
tert.butyl hexahydro-2-(2-acetylthioethyl)-2-methyl-3-oxo-1H-pyrazolo[1,2-a]pyridazine-5-carboxylate.

In accordance with the process of the invention, the pyrazolopyridazine derivatives of formula I and the salts of the compounds of formula I wherein $R^1$ is carboxy and/or $R^2$ is hydroxy with pharmaceutically acceptable bases, are prepared as follows:

(a) to prepare a compound of formula I wherein B is carbonyl, $R^1$ lower alkoxycarbonyl or lower alkanoylthio, $R^2$ is lower alkoxy and a single-bond is present in the 6,7-position, reacting a compound of the formula

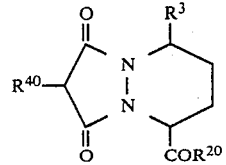

wherein $R^3$ is as previously described, $R^{20}$ is lower alkoxy and $R^{40}$ is hydrogen, lower alkyl, aryl or aryl-(lower alkyl)-, with a compound of the formula $$R^{11}—A—X \qquad \text{III}$$

wherein A is as previously described, $R^{11}$ is lower alkoxycarbonyl or lower alkanoylthio, and X is a leaving atom or group,or (b) to prepare a compound of formula I wherein $R^1$ is halogen, appropriately halogenating a compound of the formula

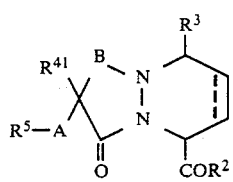

wherein A, B, $R^2$, $R^3$ and the broken line are as previously described, $R^5$ is hydroxy and $R^{41}$ is hydrogen, lower alkyl, aryl or aryl-(lower alkyl)- or a group of the formula —A—$R^5$, in which A and $R^5$ are as described above, or (e) to prepare a compound of formula I wherein B is methylene, $R^1$ is halogen and $R^2$ is lower alkoxy, cyclizing a compound of the formula

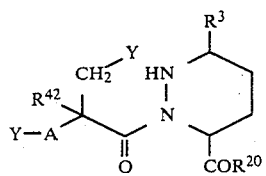

wherein A, $R^3$ and $R^{20}$ are as previously described, Y is halogen and $R^{42}$ is hydrogen, lower alkyl, aryl or aryl-(lower alkyl)-or a group of the formula —A—Y, in which A and Y are as described above, or (d) to prepare a compound of formula I wherein $R^1$ is lower alkoxycarbonyl, replacing the halogen in a corresponding compound of formula I wherein $R^1$ is halogen by lower alkoxycarbonyl in a known manner, (e) to prepare a compound of formula I wherein $R^1$ is lower alkanoylthio or aryl-(lower alkylthio)-, reacting a corresponding compound of formula I wherein $R^1$ is halogen or a compound of the formula

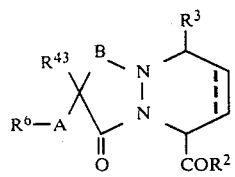

wherein A, B, $R^2$, $R^3$ and the broken line are as previously described, $R^6$ is lower alkylsulfonyloxy or arylsulfonyloxy and $R^{43}$ is hydrogen, lower alkyl, aryl or aryl-(lower alkyl)-or a group of the formula $-A-R^6$, in which A and $R^6$ are as described above, with a compound of the formula $$R^7-SH \qquad \qquad VII$$

wherein $R^7$ is lower alkanoyl or aryl-(lower alkyl), or (f) to prepare a compound of formula I wherein $R^1$ is mercapto, cleaving the lower alkanoyl or aryl-(lower alkyl)-from a corresponding compound of formula I wherein $R^1$ is lower alkanoylthio or aryl-(lower alkylthio)-, or (g) to prepare a compound of formula I wherein B is carbonyl, $R^1$ is halogen, carboxyl, lower alkoxycarbonyl or hydroxyaminocarbonyl and a single-bond is present in the 6,7-position, catalytically hydrogenating a corresponding compound of formula I wherein a double-bond is present in the 6,7-position, or (h) to prepare a compound of formula I wherein $R^1$ hydroxyaminocarbonyl, reacting a corresponding compound of formula I wherein $R^1$ is lower alkoxycarbonyl or a compound of the formula

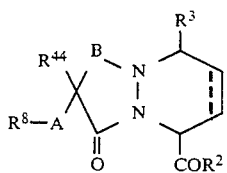

wherein A, B, $R^2$, $R^3$ and the broken line are as previously described, $R^8$ is aryloxycarbonyl and $R^{44}$ is hydrogen, lower alkyl, aryl or aryl-(lower alkyl)- or a group of the formula $-A-R^8$, in which A and $R^8$ are as described above, with hydroxylamine, or (i) to prepare a compound of formula I wherein $R^1$ is lower alkoxycarbonyl and/or $R^2$ is lower alkoxy, esterifying a corresponding compound of formula I wherein $R^1$ is carboxy and/or $R^2$ is hydroxy, or (j) to prepare a compound of formula I wherein $R^2$ is amino, amidating a compound of formula I wherein $R^2$ is hydroxy, or (k) to prepare a compound of formula I wherein $R^1$ carboxy and/or $R^2$ is hydroxy, treating a compound of formula I wherein $R^1$ is lower alkoxycarbonyl and/or $R^2$ is lower alkoxy with an acid or a base, or (l) to prepare a compound of formula I wherein B is carbonyl, $R^1$ is carboxyl, $R^2$ is lower alkoxy and a single-bond is present in the 6,7-position, debenzylating a compound of the formula

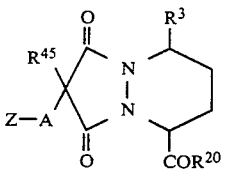

wherein A, $R^3$ and $R^{20}$ are as previously described, Z is benzyloxycarbonyl and $R^{45}$ is hydrogen, lower alkyl, aryl or aryl-(lower alkyl)- or a group of the formula $-A-Z$, in which A and Z are as described above, or (m) to prepare a compound of formula I wherein $R^1$ is carboxy, oxidizing a compound of formula IV hereinbefore, and (n) if desired, separating a mixture of diastereoisomers obtained into the diastereoisomer racemates, and/or (o) if desired, resolving a racemate obtained into its two antipodes, and/or (p) if desired, converting a compound of formula I wherein $R^1$ is carboxy and/or $R^2$ is hydroxy into a salt with a pharmaceutically acceptable base.

The leaving atom or group denoted by X in a compound of formula III can be any conventional leaving atom or group; for example, chlorine, bromine or iodine, or a lower alkylsulfonyloxy, for example, methanesulfonyloxy- or an arylsulfonyloxy, for example, p-toluenesulfonyloxy. Preferably, X is bromine.

The reaction of a compound of formula II with a compound of formula III in accordance with process embodiment (a) is conveniently carried out in the presence of a base and in an inert organic solvent. For example, the reaction can be carried out using an alkali metal lower alkoxide in the corresponding lower alkanol such as, sodium ethoxide in ethanol or using an alkali metal hydride, such as, sodium hydride in dimethylformamide. The temperature at which this reaction is carried out is not critical; when an alkali metal lower alkoxide is used as the base the reaction is conveniently carried out at about room temperature and when an alkali metal hydride is used as the base the reaction is conveniently carried out at an elevated temperature.

When a compound of formula II wherein $R^{40}$ is hydrogen is used as the starting material, there may be obtained in certain circumstances a mixture of 2-monosubstituted and 2,2-disubstituted compounds of formula I which can be readily separated by known procedures.

The halogenation of a compound of formula IV in accordance with process embodiment (b) can be carried out in a known manner. For example, the halogenation can be carried out by treating a compound of formula IV with a halogenating agent, such as, phosphorus trichloride, phosphorus pentachloride, phosphorus tribromide, thionyl chloride or the like. This halogenation method is expediently carried out in any ether, for example, diethyl ether and the like, and at a temperature in the range of between $-10°$ C. and $+30°$ C., preferably at about room temperature. In a preferred aspect, however, a compound of formula IV is first treated with a sulfonylating agent, for example, a lower alkanesulfonyl halide, such as, methanesulfonyl chloride or an arylsulfonyl halide, such as, p-toluenesulfonyl chloride, conveniently in the presence of a tertiary organic base, such as, pyridine and the sulfonyloxy group in the resulting compound is replaced by iodine by treatment with an alkali metal iodine, preferably sodium iodide, conveniently in an inert organic solvent such as a di(lower alkyl) ketone, for example, acetone, at an elevated temperature, for example, the reflux temperature of the reaction mixture.

The cyclization of a compound of formula IV in accordance with process embodiment (c) can be carried out in a known manner; for example, by treatment with a suitable organic acid such as acetic acid. It has been found to be convenient to carry out the cyclization in situ; that is to say, without isolating the compound of formula V from the medium in which it is prepared.

Process embodiment (d) can be carried out in a known manner. For example, a compound for formula I wherein $R^1$ is halogen can be heated with an alkali metal cyanide, especially potassium cyanide, in aqueous-alcoholic solution, especially aqueous-ethanolic solution, and the resulting nitrile can be heated with concentrated sulfuric acid or concentrated hydrochloric acid in an appropriate lower alkanol. There is thus obtained a desired compound of formula I wherein $R^1$ is lower alkoxycarbonyl. Again, for example, a compound of formula I wherein $R^1$ is halogen can be converted into a corresponding compound of formula I wherein $R^1$ is lower alkoxycarbonyl using a malonate or the like in a known manner.

The reaction of a compound of formula I wherein $R^1$ is halogen or a compound of formula VI with a compound of formula VII in accordance with process embodiment (e) is preferably carried out in the presence of a base and in an inert solvent. Included among the bases which can be used are alkali metal hydroxides, for example, sodium hydroxide and potassium hydroxide; alkali metal hydrides, for example, sodium hydride and potassium hydride; alkali metal lower alkoxides, for example, sodium methoxide, sodium ethoxide and the like; and alkali metal carbonates, for example, sodium carbonate and potassium carbonate. When $R^7$, in the compound of formula VII, is lower alkanoyl suitable solvents are di(lower alkyl) ketones, for example, acetone, and dimethylformamide or, when an alkali metal carbonate is used as the base, a mixture of water and a chlorinated hydrocarbon, for example, methylene chloride, or a mixture of water and ethyl acetate. When $R^7$, in the compound of formula VII, is aryl-(lower alkyl)-, suitable solvents are water, dimethylformamide and the like. It may be expedient to use a compound of formula VII wherein $R^7$ is lower alkanoyl in the form of an alkali metal salt, for example, the potassium salt, and, when $R^1$ in the compound of formula I is other than iodine, to carry out the reaction in the presence of a catalytic amount of an alkali metal iodide, for example, potassium iodide. The temperature at which the reaction is carried out is not critical and the reaction can be carried out at a temperature in the range of from about 10° C. to the reflux temperature of the reaction mixture.

The cleavage in accordance with process embodiment (f) can be carried out in a known manner; the particular cleavage method depending on the nature of the group to be cleaved. For example, when a lower alkanoyl group is to be cleaved, the cleavage can be carried out using an aqueous alkali metal hydroxide, for example, aqueous sodium hydroxide or aqueous potassium hydroxide, aqueous ammonia, a lower alkanol, for example, methanol, in the presence of the corresponding alkali metal lower alkoxide, for example, sodium methoxide, or a mineral acid such as hydrochloric acid, conveniently at an elevated temperature. The use of aqueous ammonia is preferred. Again, for example, when an aryl-(lower alkyl) group is to be cleaved, the cleavage can be carried out using sodium in liquid ammonia.

In accordance with process embodiment (g), a compound of formula I wherein B is carbonyl and a double-bond is present in the 6,7-position is catalytically hydrogenated. Suitable catalysts which may be used are noble metal catalysts such as, for example, palladium, platinum, ruthenium, rhodium and Raney nickel. The catalyst may be supported on a suitable carrier material, for example, palladium-on-carbon, rhodium-on-aluminum and the like. The catalytic hydrogenation can be carried out in a conventional inert organic solvent such as, an aromatic hydrocarbon, for example, benzene, toluene, xylene and the like; a lower alkanol, for example, methanol, ethanol and the like; or an ether, for example, dioxane and the like. The catalytic hydrogenation is advantageously carried out at room temperature and at atmospheric pressure.

In accordance with process embodiment (h), a compound of formula I wherein $R^1$ is lower alkoxycarbonyl or a compound of formula VIII is reacted with hydroxylamine. The reaction is expediently carried out in an inert organic solvent such as a lower alkanol, especially methanol. Although the reaction can be carried out at a temperature in the range of between 0° C. and the reflux temperature of the reaction mixture, it is preferably carried out at about room temperature. The hydroxylamine can be used in the form of an acid addition salt, for example, the hydrochloride, in which case a suitable base, for example, an alkali metal hydroxide, particularly potassium hydroxide, is included in the reaction mixture.

The esterification of a compound of formula I in accordance with process embodiment (i) can be carried out in a known manner. For example, the esterification can be carried out by reacting a compound of formula I wherein $R^1$ is carboxy and/or $R^2$ is hydroxy with a lower alkanol, for example, methanol, ethanol and the like, in the presence of an appropriate acid, for example, a mineral acid such as hydrochloric acid, or with a suitable diazoalkane, such as, for example, diazomethane. Alternatively, a compound of formula I wherein $R^1$ is carboxy and/or $R^2$ is hydroxy can first be converted in a known manner, for example, by treatment with a chlorinating agent such as thionyl chloride, phosphorus trichloride or phosphorus pentachloride, into a corresponding acid chloride which is then reacted, also in a known manner, with a lower alkanol. A tert.butyl ester can also be obtained by reacting a compound of formula I wherein $R^1$ is carboxy and/or $R^2$ hydroxy with isobutene in the presence of sulfuric acid.

The amidation in accordance with process embodiment (j) can be carried out in a known manner. For example, a compound of formula I wherein $R^2$ is hydroxy can be converted in the manner described in the preceding paragraph into a corresponding acid chloride which yields a desired compound of formula II wherein $R^2$ is amino after treatment with ammonia in a known manner.

In accordance with process embodiment (k), a compound of formula I wherein $R^1$ is lower alkoxycarbonyl and/or $R^2$ is lower alkoxy is converted into a compound of formula I wherein $R^1$ is carboxy and/or $R^2$ is hydroxy. This embodiment can be carried out in a known manner; for example, by treatment with aqueous alkali metal hydroxide such as sodium hydroxide or potassium hydroxide or an aqueous mineral acid such as hydrochloric acid, conveniently at a temperature in the range of between room temperature and the boiling point of the mixture, or, when $R^1$ is tert.butoxycarbonyl and/or $R^2$ is tert.butoxycarbonyl, by treatment with anhydrous acid.

The debenzylation in accordance with process embodiment (l) can be carried out in a conventional manner; for example, using hydrogen in the presence of a catalyst, for example, palladium/carbon, in a lower alkanol solvent, for example, methanol, at room temperature and atmospheric pressure.

The oxidation of a compound of formula IV in accordance with process embodiment (m) can be carried out according to known methods for the oxidation of alcohols to be corresponding carboxylic acids; for example, using a chromic oxidizing agent.

The compounds of formula I contain an asymmetric center at the 5-position and can therefore exist in racemic or optically active form. Compounds of formula I which contain more than one asymmetric center can exist in various diastereoisomeric forms. It will be appreciated that this invention includes within its scope all possible stereoisomers of the compounds of formula I and all possible mixtures of diastereoisomers and racemates. The separation of diastereoisomer mixtures into the diastereoisomer racemates in accordance with embodiment (n) of the present process and the resolution of racemates into the optical antipodes in accordance with embodiment (o) of the present process can be carried out according to known methods.

Compounds of formula I wherein $R^1$ is carboxy and/or $R^2$ is hydroxy can be converted into salts with pharmaceutically acceptable bases in accordance with embodiment (p) of the present process; for example, by treatment with alkali metal hydroxides, for example, sodium hydroxide and potassium hydroxide; alkaline earth metal hydroxides, for example, calcium hydroxide and magnesium hydroxide: organic bases, for example, dicyclohexylamine and the like; and basic amino acids lysine, arginine and the like.

The starting materials of formula II used in process embodiment (a) are novel and also form part of the invention. They can be prepared as illustrated in Formula Scheme I hereinafter wherein $R^3$, $R^{20}$, $R^{40}$ and Z are as previously described and $R^9$ is lower alkyl:

Formula Scheme I

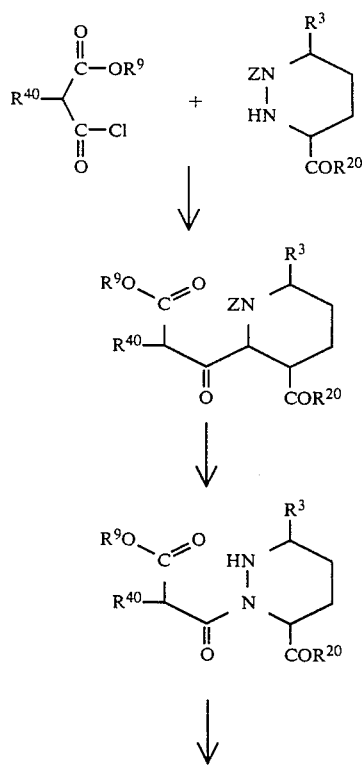

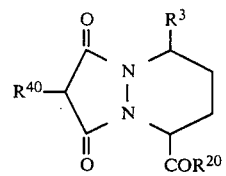

The compounds of formulas X and XI in Formula Scheme I are known compounds or analogues of known compounds which can be prepared in a similar manner to the known compounds.

The reaction of a compound of formula X with a compound of formula XI to give a compound of formula XII can be carried out under the conditions of a Schotten-Baumann reaction, namely in the presence of an inert organic solvent, for example, a halogenated hydrocarbon such as methylene chloride, and in the presence of dilute sodium hydroxide at about room temperature.

In the next step, the benzyloxycarbonyl group denoted by Z is cleaved from a compound of formula XII. This cleavage is suitably carried out using hydrogen in the presence of a catalyst such as palladium/carbon at room temperature and atmsopheric pressure.

Finally, a desired starting material of formula II is obtained by cyclizing a compound of formula XIII. This cyclization can be carried out in a known manner; for example, by heating in the presence of a suitable organic acid such as acetic acid.

The starting materials of formula IV used in process embodiment (b) are novel and also form part of the invention.

The starting materials of formula IV wherein B is carbonyl can be prepared as illustrated in Formula Scheme II hereinafter in which A, $R^2$, $R^3$, $R^5$, $R^9$ and $R^{41}$ are as previously described and $R^{10}$ is hydroxy protected in the form of a readily cleavable ether group, for example, benzyloxy, tetrahydropyranyloxy and the like.

Formula Scheme II

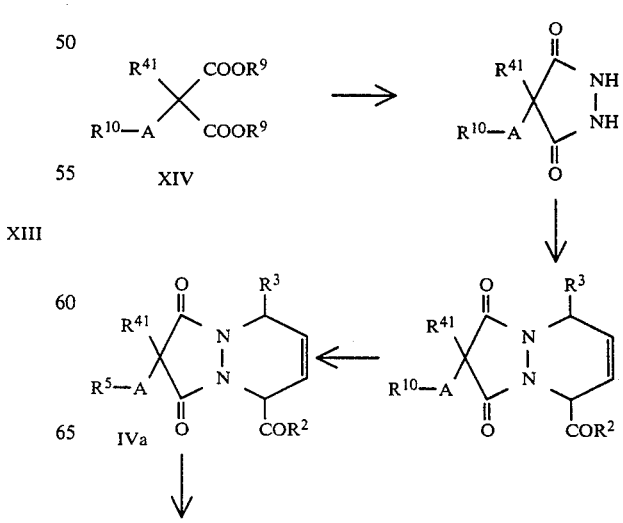

-continued
Formula Scheme II

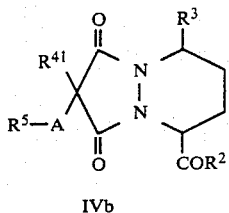

IVb

With reference to Formula Scheme II, in the first step a diester of formula XIV, which is a known compound or an analogue of a known compound, is reacted with hydrazine to give a pyrazolidinedione derivative of formula XV. This reaction is preferably carried out by heating a mixture of the diester and anhydrous hydrazine at an elevated temperature, for example, the reflux temperature of the reaction mixture.

In the next step, a pyrazolidinedione derivative of formula XV is converted into a compound of formula XVI by reaction under oxidizing conditions with a compound of the formula

 XVII wherein $R^2$ and $R^3$ are as previously described.

The oxidizing conditions required for the reaction of a pyrazolidinedione derivative of formula XV with a compound of formula XVII can suitably be provided by including an oxidizing agent such as lead tetraacetate, tert.butyl hypochlorite or the like in the reaction mixture. The reaction is suitably carried out in the presence of an inert organic solvent, examples of such solvents are aromatic hydrocarbons, for example, benzene, toluene and the like, halogenated hydrocarbons, for example, dichloromethane, chloroform, chlorobenzene and the like; di (lower alkyl) ketones, for example, acetone, methyl ethyl ketone and the like; ethers, for example, diethyl ether, dioxane, tetrahydrofuran and the like; acetonitrile; ethyl acetate; and the like. The temperature at which the reaction is carried out is not critical, but room temperature is preferred.

A starting material of formula IVa is obtained from a compound of formula XVI by cleaving the protecting group from a compound of formula XVI. This cleavage can be carried out in a known manner; for example, by treatment with a mineral acid, for example, a hydrohalic acid such as hydrochloric acid, at about room temperature.

A starting material of formula IVa can be converted into a starting material of formula IVb by catalytically hydrogenating the 6,7-double bond in a manner analogous to that described in connection with process embodiment (g) provided by this invention.

The starting materials of formula IV wherein B is methylene can be prepared, for example, by catalytically hydrogenating a mixture of a compound of formula XI hereinbefore and a compound of the formula

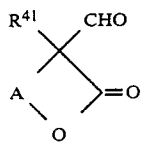 XVIII wherein A and $R^{41}$ are as previously described, in a conventional inert organic solvent under neutral or acidic conditions, there being obtained a compound of the formula

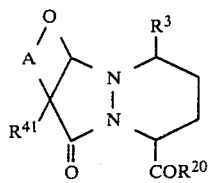 XIX wherein A, $R^3$, $R^{20}$ and $R^{41}$ are as previously described, when neutral conditions are used and a compound of the formula

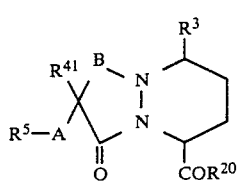 IVc wherein B, $R^3$, $R^5$, $R^{20}$ and $R^{21}$ are as previously described, when acidic conditions are used.

A compound of formula XIX is converted by catalytic hydrogenation under acidic conditions.

The catalyst used in the aforementioned catalytic hydrogenations is preferably a palladium catalyst such as palladium-on-carbon. When the catalytic hydrogenation is carried out under neutral conditions, the inert organic solvent is preferably a lower alkanol such as methanol, ethanol and the like, and when the catalytic hydrogenation is carried out under acidic conditions the inert organic solvent is preferably dioxane or the like. The acidic conditions can be provided in a conventional manner; for example, by including hydrochloric acid in the mixture. The catalytic hydrogenations can suitably be carried out at room temperature and atmospheric pressure.

If desired, the lower alkoxy group denoted by $R^{20}$ in a compound of formula IVc can be replaced by a hydroxy group or an amino group in a known manner, for example, as described earlier.

The starting materials of formula V used in process embodiment (c) are novel and also form part of the invention. They can be prepared, for example, by reacting a compound of the formula

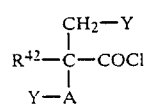 XX wherein A, $R^{42}$ and Y are as previously described, with a compound of formula XI hereinbefore and cleaving the benzyloxycarbonyl group from the resulting compound of the formula

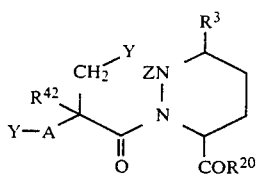

XXI wherein A, $R^3$, $R^{42}$, $R^{20}$, Y and Z are as previously described.

The reaction of a compound of formula XX, which is a known compound or an analogue of a known compound, with a compound of formula XI can be carried out in a conventional manner; for example, in the presence of an inert organic solvent, for example, a halogenated hydrocarbon such as methylene chloride, and in the presence of an acid-binding agent such as an alkali metal bicarbonate, for example, sodium bicarbonate, at about room temperature.

The cleavage of the benzyloxycarbonyl group from a compound of formula XXI can be carried out as described earlier in connection with the conversion of a compound of formula XII into a compound of formula XIII.

The starting materials of formula VI used in process embodiment (e) are novel and also form part of the invention. They can be prepared, for example, by reacting a compound of formula IV hereinbefore with an appropriate alkylsulfonyl halide, for example, methanesulfonyl chloride, or arylsulfonyl halide, for example, paratoluenesulfonyl chloride, in a known manner.

The starting materials of formula VIII used in process embodiment (h) are novel and also form part of the invention. They can be prepared, for example, in a manner analogous to that described herein for the preparation of compounds of formula I wherein $R^1$ is lower alkoxycarbonyl; for example, by reacting a compound of formula II with a compound corresponding to formula III but in which $R^{11}$ is aryloxycarbonyl.

The starting materials of formula IX used in process embodiment (1) are novel and also form part of the invention. They can be prepared, for example, by reacting a compound of formula II with a compound corresponding to formula III but in which $R^{11}$ is benzyloxycarbonyl, this reaction is carried out in a manner analogous to that described earlier in connection with process embodiment (a).

The pyrazolopyridazine derivatives of formula I provided by the invention are useful as medicaments, particularly as antihypertensive agents. They inhibit angiotensin converting enzyme (ACE) which brings about the conversion of angiotensin I into angiotensin II and are therefore useful in reducing or alleviating angiotensin-related hypertension.

The activity of the pyrazolopyridazine derivatives of formula I in inhibiting angiotensin converting enzyme in vitro can be determined by the following test.

The method used is based on the method of Cushman and Cheung (Biochem. Pharmacol., 20, 1637–1648) incorporating the modifications introduced by Hayakari et al. (Anal. Biochem., 84, 361–369). The substrate (hippuryl-histidyl-leucine, 2mM) is incubated with angiotensin converting enzyme, extracted from rabbit lumg, in the presence or absence of various concentrations of test substance in potassium phosphate buffer (pH 8.3; 100 mM) containing sodium chloride (300 mM) for 25 minutes at 37° C. (total value 500 μl). The reaction is terminated by the addition of 3 ml of potassium phosphate buffer (pH 8.3; 200 mM) at 0° C. 2,4,6-Trichloro-s-triazine (3%) in 1.5 ml of dioxane is added and the mixture is agitated until the yellow chromophore has developed fully. The samples are then centrifuged to remove any precipitate which has formed. The yellow chromophore formed by the reaction of the 2,4,6-trichloro-s-triazine with free hippuric acid is measured spectrophotometrically at 382 nm. $IC_{50}$ values are defined as the concentration of test substance which reduces by 50% the cleavage of hippurly-histidyl-leucine by angiotensin converting enzyme under the aforementioned conditions.

The results obtained in the foregoing test using representative compounds of formula I as the test substance are compiled in the following Table.

Compound A: Hexahydro-2-(2-mercaptoethyl)-2-methyl-1,3-dioxo-1H-pyrazolo[1,2-a]pyridazine-5-carboxylic acid.

Compound B: Hexahydro-2-(2-mercaptoethyl)-2-methyl-3-oxo-1H-pyrazolo[1,2-a]pyridazine-5-carboxylic acid.

Compound C: 2-Ethyl-2,3,5,8-tetrahydro-2-(2-mercaptoethyl)-1,3-dioxo-1H-pyrazolo-[1,2-a]pyridazine-5-carboxylic acid.

TABLE

| Compound | $IC_{50}$ (nanomolar) |
| --- | --- |
| A | 100 |
| B | 100 |
| C | 43 |

The pyrazolopyriadazine derivative of formula I provided by the invention can be used as medicaments in the form of pharmaceutical preparations which contain them in association with a compatible pharmaceutical carrier material. Such carrier material can be an organic or inorganic carrier material which is suitable for enteral, for example, oral, or parenteral administration, examples of such carrier materials are water, gelatin, gum arabic, lactose, starch, magnesium stearate, talc, vegetable oils, polyalkyleneglycols, petroleum jelly and the like. The pharmaceutical preparations can be made up in a solid form, for example, as tablets, dragees, suppositories or capsules, or in a liquid form, for example, as solutions, suspensions or emulsions. The pharmaceutical preparations may be subjected to standard pharmaceutical operations such as sterilization and/or may contain adjuvants such as preserving, stabilizing, wetting or emulsifying agents, salts for varying the osmotic pressure or buffers. The pharmaceutical preparations may also contain other therapeutically valuable substances.

The pyrazolopyridazine derivatives of formula I provided by the invention may be administered to adults in a daily dosage in the range of from about 0.1 mg to 100 mg, preferably in the range of from about 1 mg to 50 mg, per kilogram body weight. The daily dosage may be administered as a single dose or in divided doses. It will be appreciated that the aforementioned dosage range is given by way of example only and can be varied upwards or downwards depending on factors such as the particular pyrazolopyridazine derivative of formula I that is administered, the severity of the indication being treated and the condition of the patient, i.e., warm-blooded animal, as determined by the attending practitioner.

The Examples which follow further illustrate the invention. All temperatures are in degrees centigrade unless otherwise stated.

EXAMPLE 1

(A) A solution of 13 ml of ethylmalonyl chloride in 500 ml of dichloromethane and 210 ml of 0.5M sodium hydroxide solution were simultaneously added dropwise to a stirred solution of 28.7 of 1-benzyloxycarbonylpiperazic acid tert.butyl ester in 500 ml of dichloromethane. The mixture was stirred at room temperature for 4 hours and the layers were seperated. After chromatography of the organic layer, there were obtained 25.3g(65%) of 1-benzyl3-tert.butyl 2-(2-ethoxycarbonylacetyl)hexahydropyridazine-1,3-dicarboxylate having a melting point of 45°–47° C. (from diethyl ether/hexane).

(B) A solution of 25.3g of 1-benzyl 3-tert.butyl 2-(2-ethoxycarbonylacetyl)hexahydropyridazine-1,3-dicarboxylate in 500 ml of methanol was hydrogenated over 2.3g of 10% palladium/carbon at room temperature and under atmospheric pressure. The catalyst was removed by filtration. Evaporation of the filtrate and recrystallization of the residue from hexane gave 16.9 g (97%) of tert.butyl 2-(2-ethoxycarbonylacetyl)hexahydropyridazine-3-carboxylate having a melting point of 86°–87° C.

(C) A solution of 16.9 g of tert.butyl 2-(2-ethoxycarbonylacetyl)hexahydropyridazine-3-carboxylate in 350ml of glacial acetic acid was heated at 100° C. for 1.5 hours. Evaporation gave an oil which was chromatographed on silica gel to yield 9.45 g (66%)of tert.butyl hexahydro-1,3-dioxo-1H-pyrazolo[1,2-a]pyridazine-5-carboxylate in the form of a pale yellow solid having a melting point of 121°–122° C. (from chloroform/hexane). (D) (a) Sodium hydride (80% dispersion: 0.4 ane).

(D) (a) Sodium hydride (80% dispersion: 0.4 g)was suspended in 10 ml of dry dimethylformamide. A solution of 1.27 g of tert.butyl hexahydro-1,3-dioxo-1H-pyrazolo[12,-a]pyridazine-5-carboxylate in 10 ml of dry dimethylformamide was added and the mixture was stirred at room temperature until the evolution of gas ceased. 2.5 g of ethyl bromoacetate were added and the mixture was stirred at 20° C. for 16 hours. The solvent was removed and the residue was partitioned between 2N hydrochloric acid and dichloromethane. The organic layer was separated, dried over sodium sulfate and evaporated. The residue was chromatographed on silica gel to give 1.49 g (70%) of diethyl 5-tert.butoxycarbonyl - hexahydro - 1,3 - dioxo-1H-pyrazolo[1,2-a]-pyridazine-2,2-diacetate in the form of a colorless oil.

(D) (b) 0.43 g of sodium was dissolved in 20 ml of ethanol. A solution of 2.27 g of tert.butyl hexahydro-1,3-dioxo-1H-pyrazolo[1,2-a]pyridazine-5-carboxylate in 20 ml of ethanol was added and the mixture was heated under reflux for 2 hours. 5 g of ethyl 3-bromopropionate were added and the mixture was heated under reflux for an additional 2 hours. The solvent was removed and the residue was partitioned between dichloromethane and 2N hydrochloric acid. The organic layer was separated and evaporated. The residue was chromatographed on silica gel to give 0.37 g (9%) of tert.butyl 2,2-bis(2-ethoxycarbonylethyl)-hexahydro-1,3-dioxo-1H-pyrazolo[1,2-a]pyridazine-5-carboxylate in the form of an oil.

(D) (c) A solution of 1.27 g of tert.butyl hexahydro-1,3-dioxo-1H-pyrazolo[1,2-a]pyridazine-5-carboxyate in 10 ml of dimethylformamide was added to a suspension of 0.4 g of sodium hydride in dimethyformamide. The mixture was stirred at room temperature until the evolution of gas had ceased. 1.86 g of S-bromoethyl thioacetate were added and the mixture was heated at 75° C. for 5 hours. Working-up in the same manner as described in paragraph (D) (a) earlier gave 0.15 g (7%) of tert.butyl 2,2- bis(acetylthiomethyl)-hexahydro-1,3-dioxo-1H-pyrazolo[1,2-a]pyridazine-5-carboxylate in the form of a white solid having a melting point of 85°–86° C. (from diethyl ether/hexane).

(D) (d) In a manner analogous to that described in paragraph (D) (c) earlier, from 1.27 g of tert.butyl hexahydro-1,3-dioxo-1H-pyrazolo[1,2-a]pyridazine-5-carboxylate and 2.4 g of S-(2-bromoethyl)thiocetate there was obtained 0.09 g (4%) of tert.butyl2,2-bis(2-acetylthioethyl)-hexahydro-1,3-dioxo-1H-pyrazolo[1,2-a]pyridazine-5-carboxylate in the form of an oil. There was also isolated 0.075 g(4%) of tert.butyl2-(2-acetylthioethyl)hexahydro-1,3-dioxo-1H-pyrazolo[1,2-a]pyridazine-5-carboxylate in the form of a white solid having a melting point of 86°–88° C.(from diethyl ether).

EXAMPLE 2

(A) In a manner analogous to that described in Example 1(A), from 1-benzyloxcarbonylpiperazic acid tert.butyl ester and ethyl methylmalonyl chloride there was obtained in 36% yield 1-benzyl 3-tert.butyl 2(2-ethoxycarbonyl)-2-methylacetyl)hexahydropyridazine-1,3-dicarboxylate in the form of an oil.

(B) In a manner analogous to that described in Example 1(B), from 3.9 g of 1-benzyl 3-tert.butyl 2-(2-ethoxycarbonyl-2-methylacetyl)hexahydropyridazine-1,3-dicarboxylate there were obtained 2.6 g (95%) of tert.butyl 2-(2-ethoxycarbonyl-2-methylacetyl)hexahydropyridazine-3-carboxylate in the form of an oil.

(C) In a manner analogous to that described in Example 1(C), from 2.6 g of tert.butyl 2-(2-ethoxycarbonyl-2-methylacetyl)Hexahydropyridazine-3-carboxylate there were obtained 1.39 g (63%) of tert.butyl hexahydro-2-methyl-1,3-dioxo-1H-pyrazolo[1,2-a]-pyridazine-5-carboxylate in the form of a white solid having a melting point of 127°–128° C. (from chloroform/hexane).

(D) (a) In a manner analogous to that described in Example 1(D)(c), from 7.08 g of tert.butyl hexahydro-2-methyl-1,3-dioxo-1H-pyrazolo[1,2-a]pyridazine-5 -carboxylate and 4.98 g of S-bromoethyl thioacetate there were obtained 5.59 g (59%) of tert.butyl 2-acetylthiomethyl-hexahydro-2-methyl-1,3-dioxo-1H-pyrazolo[1,2-a]pyridazine-5-carboxylate in the form of an oily mixture of diastereomers. The diastereomers were separated by chromatography and there was obtained diastereomer A having a melting point of 78°–79° C. (from ethyl acetate/hexane) and diastereomer B in the form of a colorless oil.

(D) (b) In a manner analogous to that described in Example 1(D) (c), from5 g of tert.butyl hexahydro-2-methyl-1,3-dioxo-1H-pyrazolo[1,2a]pyridazine-5-carboxylate and 6.19 g of S-(2-bromoethyl)thioacetate there were obtained 4.22 g(61%) of tert.butyl 2-(2-acetylthioethyl)-hexahydro-2-methyl-1,3-dioxo-1H-pyrazolo[1,2-a]pyridazine-5-carboxylate in the form of an oily mixture of diastereomers. Chromatography gave diastereomer A having a melting point of 79°–80° C.(from ethyl acetate/hexane) and diastereomer B having a melting point of 67°–70° C.(from ethyl acetate/hexane).

(D) (c) In a manner analogous to that described in Example 1(D) (c), from 3.0 g of tert.butyl hexahydro-2- methyl-1,3-dioxo-1H-pyrazolo[1,2-a]pyridazine-5-carboxylate and 3.4 of S-(3-brompropyl)thioacetate there were obtained 2.18 g (51%) of tert. butyl 2-(3-acetylthiopropyl)-hexahydro-2-methyl-1,3-dioxo-1H-pyrazolo[1,2a]pyridazine-5-carboxylate in the form of an oily mixture of diastereomers. Chromatography gave diastereomer A having a melting point of 125°–128° C. (from ethyl acetate/hexane) and diastereomer B having a melting point of 94°–96° C. (from ethyl acetate/hexane).

EXAMPLE 3

1.5 g of diethyl 5-tert.butoxycarbonyl-hexahydro-1,3dioxo-1H-pyrazolo[1,2-a]pyridazine-2,2-diacetate were dissolved in 25 ml of trifluoroacetic acid and the solution was left to stand at room temperature for 1 hour. The mixture was evaporated and the residue was recrystallized from dichloromethane/hexane to give 0.73 g (56%) of diethyl 5-carboxy-hexahydro-1,3-dioxo-1H-pyrazolo[1,2-a]pyridazine-2,2-diacetate in the form of a beige solid having a melting point of 105°–108° C.

EXAMPLE 4

(A) In a manner analogous to that described in Example 1 (D) (a), from tert.butyl hexahydro-1,3-dioxo-1H-pyrazolo[1,2-a]pyridazine-5-carboxylate and benzyl bromoacetate there was obtained in 60% yield dibenzyl 5-tert.butoxycarbonyl-hexahydro-1,3-dioxo-1H-pyrazolo[1,2-a]pyridazine-2,2-diacetate in the form of a colorless oil.

(B) In a manner analogous to that described in Example 3, from dibenzyl 5-tert.butoxycarbonyl-hexahydro-1,3-dioxo-1H-pyrazolo[1,2-a]pyridazine-2,2-diacetate there was obtained dibenzyl 5-carboxy-hexahydro-1,3-dioxo-1H-pyrazolo[1,2-a]-pyridazine-2,2-diacetate in the form of a colorless oil.

(C) A solution of the acid obtained according to paragraph (B) in methanol was hydrogenated over 10% palladium-on-carbon to give 5-carboxy-hexahydro-1,3-dioxo-1H-pyrazolo[1,2-a]pyridazine-2,2-diacetic acid in the form of a colorless hygroscopic solid (from ethyl acetate/hexane.

EXAMPLE 5

In a manner analogous to that described in Example 3, from 0.3 g of tert.butyl 2-(2-acetylthioethyl)-hexahydro-2-methyl-1,3-dioxo-1H-pyrazolo[1,2-a]pyridazine-5-carboxylate (diastereomer A) there was obtained 0.25 g (98%) of 2-(2-acetylthioethyl)-hexahydro-2-methyl-1,3-dioxo-1H-pyrazolo[1,2-a]pyridazine-5-carboxylic acid (diastereomer A) in the form of a white solid having a melting point of 142°–143° C. (from ethyl acetate).

EXAMPLE 6

In a manner analogous to that described in Example 3, from 0.19 g of tert.butyl 2-(3-acetylthiopropyl)-hexahydro-2-methyl-1,3-dioxo-1H-pyrazolo[1,2-a]pyridazine-5-carboxylate (diastereomer A) there was obtained 0.1 g (62%) of 2-(3-acetylthiopropyl)-hexahydro-2-methyl-1,3-dioxo-1H-pyrazolo[1,2-a]pyridazine-5-carboxylic acid (diastereomer A) in the form of a white solid having a melting point of 160°–161° C. (from ethyl acetate/hexane).

EXAMPLE 7

(A) A mixture of 120.8 g (0.4 mol) of diethyl 2-methyl-2-[2-(tetrahydro-2-pyranyloxy)ethyl]-propane-1,3-dioate and 150 ml of anhydrous hydrazine was heated under reflux for 64 hours. The excess hydrazine was removed by distillation and the residue was recrystallized from methanol to give 60.28 g (62%) of 4-methyl-4-[2-(tetrahydro-2-pyranyloxy)-ethyl]-pyrazolidine-3,5-dione having a melting point of 179°–180° C.

(B)(a) 1.21 g (5 mmol) of 4-methyl-4-[2-(tetrahydro-2-pyranyloxy)ethyl]pyrazolidine-3,5-dione were suspended in 20 ml of dry dioxan and the suspension was stirred at room temperature under a stream of nitrogen. A solution of 0.543 g (5 mmol) of tert.butyl hypochlorite in 5 ml of dry dioxan was added over a period of 15 minutes. The resulting blue solution was filtered and the filtrate was evaporated in vacuo. The residue was dissolved in 10 ml of dry dioxan and the solution was added portionwise to a stirred solution of 0.616 g (5.5 mmol) of methyl penta-2,4-dienoate in 20 ml of dry dioxan. The blue color was allowed to fade between additions. When the addition was complete and no blue color persisted, the solution was stirred at room temperature for 1 hour. The resulting solution was evaporated in vacuo and the residue was chromatographed on silica gel. Elution with diethyl ether gave 0.52 g (29%) of methyl 2,3,5,8-tetrahydro-2-methyl-1,3-dioxo-2-[2-(tetrahydro-2-pyranyloxy)ethyl]-1H-pyrazolo[1,2-a]pyridazine-5-carboxylate having a melting point of 127.5°–128.5° C. (from diethyl ether).

(B)(b) A mixture of 14.52 g (0.06 mol) of 4-methyl-4-[2-(tetrahydro-2-pyranyloxy)ethyl]pyrazolidine-3,5-dione and 6.72 g (0.066 mol) of methyl penta-2,4-dienoate in 150 ml of dry dichloromethane was stirred at room temperature under a stream of nitrogen. A solution of 26.64 g (0.06 mol) of lead tetraacetate in 100 ml of dry dichloromethane was added dropwise, the blue color being allowed to fade between additions. When the addition was complete and no blue color persisted, the resulting suspension was filtered. The filtrate was washed with saturated aqueous sodium bicarbonate, dried over magnesium sulfate and evaporated to give 8.12 g (38%) of methyl 2,3,5,8-tetrahydro-2-methyl-1,3-dioxo-2-[2-(tetrahydro-2-pyranyloxy)ethyl]-1H-pyrazolo[1,2-a]pyridazine-5-carboxylate having a melting point of 126.5°–127.6° C. (from diethyl ether).

(C) A solution of 3.52 g (0.01 mol) of methyl 2,3,5,8-tetrahydro-2-methyl-1,3-dioxo-2[2-(tetrahydro-2-pyranyloxy)ethyl]-1H-pyrazolo[1,2-a]pyridazine-5-carboxylate in 50 ml of 1M hydrochloric acid and 50 ml of methanol was stirred at room temperature for 1.5 hours. The solvent was removed by evaporation in vacuo. The solid residue was taken up in dichloromethane, dried over magnesium sulfate and evaporated to give 2.6 g (97%) of methyl 2,3,5,8-tetrahydro-2-(2-hydroxyethyl)-2-methyl-1,3-dioxo-1H-pyrazolo[1,2-a]pyridazine-5-carboxylate having a melting point of 97°–99° C. (from diethyl ether).

(D) 3.45 g (30 mmol) of methanesulfonyl chloride were added dropwise to a stirred solution, cooled at 0° C., of 6.7 g (25 mmol) of methyl 2,3,5,8-tetrahydro-2-(2-hydroxyethyl)-2-methyl-1,3-dioxo-1H-pyrazolo[1,2-a]-pyridazine-5-carboxylate in 20 ml of dry pyridine. After 2 hours, the resulting suspension was poured on ice-/water and acidified with 2M hydrochloric acid. Extraction with dichloromethane then yielded 7.84 g (75%) of methyl 2,3,5,8-tetrahydro-2-(2-methanesulfonyloxyethyl)-2-methyl-1,3-dioxo-1H-pyrazolo[1,2-a]pyridazine-5-carboxylate having a melting point of 104°–105° C. (from diethyl ether).

(E) A mixture of 7.6 g (22 mmol) of methyl 2,3,5,8-tetrahydro-2-(2-methanesulfonyloxyethyl)-2-methyl- 1,3-dioxo-1H-pyrazolo[1,2-a]pyridazine-5-carboxylate and 6.6 g (44 mmol) of sodium iodide in 100 ml of acetone was heated under reflux for 16 hours. The resulting suspension was filtered and the filtrate was evaporated to dryness. The residue was partitioned between dichloromethane and water. The organic solution was washed with 10% aqueous sodium thiosulfate, dried over magnesium sulfate and evaporated to give 6.7 g (80%) of methyl 2,3,5,8-tetrahydro-2-(iodoethyl)-2-methyl-1,3-dioxo-1H-pyrazolo[1,2-a]-pyridazine-5-carboxylate having a melting point of 86°–87° C. (from diethyl ether).

EXAMPLE 8

A mixture of 6.43 g (17 mmol) of methyl 2,3,5,8-tetrahydro-2-(2-iodoethyl)-2-methyl-1,3-dioxo-1H-pyrazolo-[1,2-a]pyridazine-5-carboxylate and 1.94 g (17 mmol) of potassium thioacetate in 150 ml of acetone was stirred at room temperature for 5 hours. The solvent was removed by evaporation and the residue was partitioned between dichloromethane and water. The organic phase was separated, dried over magnesium sulfate and evaporated to give methyl 2-(2-acetylthioethyl)-2,3,5,8-tetrahydro-2-methyl-1,3-dioxo-1H-pyrazolo[1,2-a]pyridazine-5-carboxylate as a mixture of diastereomers. Chromatography on silica gel using diethyl ether for the elution gave 3.81 g (69%) of diastereomer A in the form of a colorless oil and 1.26 g (23%) of diastereomer B in the form of a colorless oil.

EXAMPLE 9

A solution of 0.71 g of tert.butyl 2-acetylthiomethyl-hexahydro-2-methyl1,3-dioxo-1H-pyrazolo[1,2-a]pyridazine-5-carboxylate (diastereomer A) in 10 ml of trifluoroacetic acid was left to stand at room temperature for 1 hour. The mixture was evaporated to dryness and the residue was stirred under nitrogen with 50 ml of 50:50 mixture of water and concentrated aqueous ammonia for 2 hours. The mixture was acified to pH 1 with hydrochloric acid, saturated with sodium chloride and extracted with chloroform. The chloroform extracts were dried over sodium sulfate and evaporated. The residue was recrystallized from ethyl acetate/hexane to give 0.22 g (43%) of hexahydro-2-mercaptomethyl-2-methyl-1,3-dioxo-1H-pyrazolo[1,2-a]pyridazine-5-carboxylic acid (diastereomer A) in the form of white crystals having a melting point of 209°–211° C.

EXAMPLE 10

In a manner analogous to that described in Example 9, from tert.butyl 2-(2-acetylthioethyl)-hexahydro-2-methyl-1,3-dioxo-1H-pyrazolo[1,2-a]pyridazine-5-carboxylate (diastereomer A) there was obtained in 48% yield hexahydro-2-(2-mercaptoethyl)-2-methyl-1,3-dioxo-1H-pyrazolo[1,2-a]pyridazine-5-carboxylic acid (diastereomer A) having a melting point of 170°–173° C. (from ethyl acetate/hexane).

EXAMPLE 11

In a manner analogous to that described in Example 9, from tert.butyl 2-(2-acetylthioethyl)-hexahydro-2-methyl-1,3-dioxo-1H-pyrazolo[1,2-a]pyridazine-5-carboxylate (diastereomer B) there was obtained in 62% yield hexahydro-2-(2-mercaptoethyl)-2-methyl-1,3-dioxo-1H-pyrazolo[1,2-a]pyridazine-5-carboxylic acid (diastereomer B) having a melting point of 165°–168° C. (from ethyl acetate/hexane).

EXAMPLE 12

In a manner analogous to that described in Example 9, from tert.butyl 2-(2-acetylthioethyl)-hexahydro-1,3-dioxo-1H-pyrazolo[1,2-a]pyridazine-5-carboxylate there was obtained in 53% yield hexahydro-2-(2-mercaptoethyl)-1,3-dioxo-1H-pyrazolo[1,2-a]pyridazine-5-carboxylic acid in the form of a hygroscopic solid.

EXAMPLE 13

In a manner analogous to that described in Example 9, from tert.butyl 2,2-bis(2-acetylthioethyl)-hexahydro-1,3-dioxo-1H-pyrazolo[1,2-a]pyridine-5-carboxylate there was obtained in 90% yield hexahydro-2,2-bis(2-mercaptoethyl)-1,3-dioxo-1H-pyrazolo[1,2-a]pyridazine-5-carboxylic acid in the form of a colorless foam.

EXAMPLE 14

(A) In a manner analogous to that described in Example 1(A), from 6.5 g of 1-benzyloxycarbonylpiperazic acid tert.butyl ester and 5 g of ethyl ethylmalonyl chloride there were obtained 5.5 g (54%) of 1-benzyl 3-tert.butyl 2-(2-ethoxycarbonylbutyryl)hexahydropyridazine-1,3-dicarboxylate in the form of an oil.

(B) In a manner analogous to that described in Example 1(B), from 5.5 g of 1-benzyl 3-tert.butyl 2-(2-ethoxycarbonylbutyryl)hexahydropyridazine-1,3-dicarboxylate there were obtained 2.7 g (69%) of tert.butyl 2-(2-ethoxycarbonylbutyryl)-hexahydropyridazine-3-carboxylate in the form of a light tan solid having a melting point of 78°–79° C. (from hexane).

(C) In a manner analogous to that described in Example 1(C), from 1.1 g of tert.butyl 2-(2-ethoxycarbonylbutyryl)-hexahydropyridazine-3-carboxylate there was obtained 0.75 g (79%) of tert.butyl 2-ethyl-hexahydro-1,3-dioxo-1H-pyrazolo[1,2-a]pyridazine-5-carboxylate in the form of a light tan solid having a melting point of 93°–95° C. (from chloroform/hexane).

(D) In a manner analogous to that described in Example 1(D)(c), from 4 g of tert.butyl 2-ethyl-hexahydro-1,3-dioxo-1H-pyrazolo[1,2-a]pyridazine-5-carboxylate and 5.43 g of S-(2-bromoethyl) thioacetate there was obtained tert.butyl 2-(2-acetylthioethyl)-2-ethyl-hexahydro-1,3-dioxo-1H-pyrazolo[1,2-a]pyridazine-5-carboxylate as a mixture of diastereomers. Chromatography gave 1.1 g (20%) of diastereomer A having a melting point of 82°–84° C. (from diethyl ether/hexane) and 0.4 g (7%) of diastereomer B in the form of a colorless oil.

(E) In a manner analogous to that described in Example 3, from 1.1 g of tert.butyl 2-(2-acetylthioethyl)-2-ethyl-hexahydro-1,3-dioxo-1H-pyrazolo[1,2-a]-pyridazine-5-carboxylate (diastereomer A) there was obtained 0.7 g (75%) of 2-(2-acetylthioethyl)-2-ethyl-hexahydro-1,3-dioxo-1H-pyrazolo[1,2-a]pyridazine-5-carboxylic acid (diastereomer A) in the form of a light tan solid having a melting point of 110°–111° C. (from ethyl acetate/hexane).

(F) 0.33 g of 2-(2-acetylthioethyl)-2-ethyl-hexahydro-1,3-dioxo-1H-pyrazolo[1,2-a]pyridazine-5-carboxylic acid was heated under reflux for 0.5 hour with 10 ml of 2M hydrochloric acid. After evaporation, the residue was dissolved in dichloromethane, the solution was dried over magnesium sulfate and then evaporated to give 0.27 g (94%) of 2-ethyl-hexahydro-2-(2-mercaptoethyl)-1,3-dioxo-1H-pyrazolo[1,2-a]pyridazine-5-carboxylic acid in the form of a colorless foam.

EXAMPLE 15

1.1 g of methyl 2-(2-acetylthioethyl)-2,3,5,8-tetrahydro-2-methyl-1,3-dioxo-1H-pyrazolo[1,2-a]pyridazine-5-carboxylate (diastereomer A) were heated under reflux for 3 hours with 25 ml of 2 M hydrochloric acid. After evaporation, the residue was taken up in dichloromethane, the solution was dried over magnesium sulfate and then evaporated. There was obtained 0.35 g (38%) of 2,3,5,8-tetrahydro-2-(2-mercaptoethyl)-2-methyl-1,3-dioxo-1H-pyrazolo[1,2-a]pyridazine-5-carboxylic acid (diastereomer A) in the form of a white solid having a melting point of 113°–114° C. (from diethyl ether/petroleum ether).

EXAMPLE 16

In a manner analogous to that described in Example 15, from 0.98 g of methyl 2-(2-acetylthioethyl)-2,3,5,8-tetrahydro-2-methyl-1,3-dioxo-1H-pyrazolo[1,2-a]pyridazine-5-carboxylate (diastereomer B) there was obtained 0.56 g (69%) of 2,3,5,8-tetrahydro-2-(2-mercaptoethyl)-2-methyl-1,3-dioxo-1H-pyrazolo[1,2-a]pyridazine-5-carboxylic acid (diastereomer B) in the form of a pale yellow foam.

EXAMPLE 17

(A) In a manner analogous to that described in Example 7(A), from 66.5 g of diethyl 2-benzyl-2-[2-(tetrahydro-2-pyranyloxy)ethyl]-propane-1,3-dioate and 110 ml of anhydrous hydrazine there were obtained 34.6 g (62%) of 4-benzyl-4-[2-(tetrahydro-2-pyranyloxy)ethyl]pyrazolidine-3,5-dione in the form of a white solid having a melting point of 198°–200° C. (from methanol).

(B) In a manner analogous to that described in Example 7(B) (b), from 2.7 g of 4-benzyl-4-[2-(tetrahydro-2-pyranyloxy)ethyl]pyrazolidine-3,5-dione and 1.05 g of methyl penta-2,4-dienoate there were obtained 1.2 g (34%) of methyl 2-benzyl-2,3,5,8-tetrahydro-1,3-dioxo-2-[2-(tetrahydro-2-pyranyloxy)ethyl]-1H-pyrazolo[1,2-a]pyridazine-5-carboxylate in the form of a white solid having a melting point of 113°–114° C. (from diethyl ether).

(C) In a manner analogous to that described in Example 7(C), from 1 g of methyl 2-benzyl-2,3,5,8-tetrahydro-1,3-dioxo-2-[2-(tetrahydro-2-pyranyloxy)ethyl]-1H-pyrazolo[1,2-a]pyridazine-5-carboxylate there was obtained 0.71 g (88%) of methyl 2-benzyl-2,3,5,8-tetrahydro-2-(2-hydroxyethyl)-1,3-dioxo-1H-pyrazolo[1,2-a]pyridazine-5-carboxylate in the form of a white solid having a melting point of 148°–149° C. (from diethyl ether).

(D) In a manner analogous to that described in Example 7(D), from 6.4 g of methyl 2-benzyl-2,3,5,8-tetrahydro-2-(2-hydroxethyl)-1,3-dioxo-1H-pyrazolo[1,2-a]pyridazine-5-carboxylate and 2.6 g of methanesulfonyl chloride there were obtained 5.5 g (71%) of methyl 2-benzyl-2,3,5,8-tetrahydro-2-(2-methanesulfonyloxyethyl(-1,3-dioxo-1H-pyrazolo[1,2-a]pyridazine-5-carboxylate in the form of a white solid having a melting point of 161°–163° C. (from diethyl ether).

(E) In a manner analogous to that described in Example 7(E), from 5.9 g of methyl 2-benzyl-2,3,5,8-tetrahydro-2-(2-methanesulfonyloxyethyl)-1,3-dioxo-1H-pyrazolo[1,2-a]pyridazine-5-carboxylate and 4.2 g of sodium iodide there were obtained 3.25 g (51%) of methyl 2-benzyl-2,3,5,8-tetrahydro-2-(2-iodoethyl)-1,3-dioxo-1H-pyrazolo[1,2-a]pyridazine-5-carboxylate in the form of a white solid having a melting point of 90°–92° C. (from diethyl ether).

(F) (a) A mixture of 5.2 g of methyl 2-benzyl-2,3,5,8-tetrahydro-2-(2-iodoethyl)-1,3-dioxo-1H-pyrazolo[1,2-a]pyridazine-5-carboxylate and 1.31 g of potassium thioacetate in 150 ml of acetone was stirred at room temperature for 8 hours. The solvent was removed by evaporation and the residue was partitioned between dichloromethane and water. The organic phase was separated, dried over magnesium sulfate and evaporated to give methyl 2-(2-acetylthioethyl)-2-benzyl-2,3,5,8-tetrahydro-1,3-dioxo-1H-pyrazolo[1,2-a]pyridazine-5-carboxylate as a mixture of diastereomers. Trituration with diethyl ether gave 3.5 g of diasteremoer B in the form of a white solid having a melting point of 161°–162° C. (from ethylacetate).

(F) (b) A mixture of 0.5 g of methyl 2-benzyl-2,3,5,8-tetrahydro-2-(2-iodoethyl)-1,3-dioxo-1H-pyrazolo[1,2-a]pyridazine-5-carboxylate, 0.15 g of potassium acetate and 0.1 g of thioacetic acid in 40 ml of acetone was stirred at room temperature for 5 hours. The solvent was removed by evaporation and the residue was partitioned between dichloromethane and water. The organic phase was separated, dried over magnesium sulfate and evaporated to give 0.4 g (90%) of methyl 2-(2-acetylthioethyl)-2-benzyl-2,3,5,8-tetrahydro-1,3-dioxo-1H-pyrazolo[1,2-a]pyridazine-5-carboxylate (diastereomer A) in the form of a pale yellow oil.

(G) (a) In a manner analogous to that described in Example 15, from 1.6 g of methyl 2-(2-acetylthioethyl)-2-benzyl-2,3,5,8-tetrahydro-1,3-dioxo-1H-pyrazolo[1,2-a]pyridazine-5-carboxylate (diastereomer B) there was obtained 0.68 g (49%) of 2-benzyl-2,3,5,8-tetrahydro-2-(2-mercaptoethyl)-1,3-dioxo-1H-pyrazolo[1,2-a]pyridazine-5-carboxylic acid (diastereomer B) in the form of a white solid having a melting point of 151°–154° C. (from ethyl acetate.

(G) (b) In a manner analogous to that described in Example 15, from 0.8 g of methyl 2-(2-acetylthioethyl)-2-benzyl-2,3,5,8-tetrahydro-1,3-dioxo-1H-pyrazolo[1,2-a]pyridazine-5-carboxylate (diastereomer A) there was obtained 0.25 g (36%) of 2-benzyl-2,3,5,8-tetrahyro-2-(2-mercaptoethyl)-1,3-dioxo-1H-pyrazolo[1,2-a]-pyridazine-5-carboxylic acid (diastereomer A) in the form of a white solid having a melting point of 184°–184° C. (from diethyl ether).

EXAMPLE 18

(A) In a manner analogous to that described in Example 7(A), from 6.32 g of diethyl 2ethyl-2-[2-(tetrahydro-2-pyranyloxy)ethyl]-propane-1,3-dioate and 10.5 ml of anhydrous hyrazine there were obtained 2.3 g (45%) of 4-ethyl-4-[2-(tetrahydro-2-pyranyloxy)ethyl]pyrazolidine-3,5-dione in the form of a white solid having a melting point of 188°–191° C. (from mentanol).

(B) In a manner analogous to that described in Example 7(B) (b), from 7.75 g of 4-ethyl-4-[2-(tetrahydro-2-pyranyloxy)ethyl]pyrazolidine-3,5-dione and 3.7 g of methyl penta-2,4-dienoate there were obtained 6.49 g (59%) of methyl 2-ethyl-2,3,5,8-tetrahydro-1,3-dioxo-2-[2-(tetrahydro-2-pyranyloxy)ethyl]-1H-pyrazolo[1,2-a]pyridazine-5-carboxylate in the form of a white solid having a melting point of 96°–97° C. (from diethyl ether).

(C) In a manner analogous to that described in Example 7(C), from 16.5 g of methyl 2-ethyl-2,3,5,8-tetrahydro-1,3-dioxo-2-[-(tetrahydro-2-pyranyloxy)ethyl]-1H-pyrazolo [1,2-a]pyridazine-5-carboxylate there were obtained 6.88 g (54%) of methyl 2-ethyl-2,3,5,8-tetrahydro-2-(2-hydroxyethyl)-1,3-dioxo-1H-pyrazolo[1,2-a]pyridazine-5-carboxylate in the form of a white solid having a melting point of 87°–92° C. (from diethyl ether).

(D) In a manner analogous to that described in Example 7(D), from 6.30 g of methyl 2-ethyl-2,3,5,8-tetrahydro-2-(2-hydroxyethyl)-1,3-dioxo-1H-pyrazolo[1,2-a]pyridazine-5-carboxylate there were obtained 5.14 g (65%) of methyl 2-ethyl-2,3,5,8-tetrahydro-2-(2-methanesulfonyloxyethyl)-1,3-dioxo-1H-pyrazolo[1,2-a]pyridazine-5-carboxylate in the form of a white solid having a melting point of 94°–96° C. (from diethyl ether).

(E) In a manner analogous to that described in Example 7 (E), from 8.22 g of methyl 2-ethyl-2,3,5,8-tetrahydro-2-(2-methanesulfonyloxyethyl-1,3-dioxo-1H-pyrazolo[1,2-a]pryidazine-5-carboxylate there were obtained 5 g (55%) of methyl 2-ethyl-2,3,5,8-tetrahydro-2-(2-iodoethyl)-1,3-dioxo-1H-pyrazolo[1,2a]pyridazine-5-carboxylate in the form of a white solid having a melting point of 95°–97° C. (from diethyl ether/hexane).

(F) In a manner analogous to that described in Example 17(F)(b), from 3.25 g of methyl 2-ethyl-2,3,5,8-tetrahydro-2-(2-iodoethyl)-1,3-dioxo-1H-pyrazolo[1,2-a]pyridazine--5-carboxylate there were obtained 2.5 g (89%) of methyl 2-(2-acetylthioethyl)-2-ethyl-2,3,5,8-tetrahydro-1,3-dioxo- 1H-pyrazolo[1,2-a]pyridazine-5-carboxylate (diastereomer A) in the form of a pale yellow oil.

(G) In a manner analogous to that described in Example 15, from 0.5 g of methyl 2-(2-acetylthioethyl)-2-ethyl-2,3,5,8-tetrahydro-1,3-dioxo-1H-pyrazolo[1,2-a]pyradazine-5-carboxy-late (diastereomer A) there was obtained 0.21 g (49%) of 2-ethyl-2,3,5,8-tetrahydro-2-(2-mercaptoethyl)-1,3-dioxo-1H-pyrazolo[1.2-a]pyridazine-5-carboxylic acid (diastereomer A) in the form of a white foam.

EXAMPLE 19

(A) 1.4 g of potassium carbonate, 2.68 g of tert.butyl hexahydro-2-methyl-1,3-dioxo-1H-pyrazolo[1,2-a]pyridazine-5-carboxylate and 3.6 g of phenyl bromoacetate in 20ml of acetone were stirred under reflux for 7 hours. Filtration followed by evaporation of the filtrate yielded an oil which was chromatographed on 300 g of silica gel using 5% ethyl acetate in dichloromethane for the elution. There were obtained, after recrystallization from ethyl acetate/hexane, 1.83 g of phenyl 5-tert.butoxycarbonyl-hexahydro -2-methyl -1,3-dioxo- 1H-pyrazolo[1,2-a]pyridazine-2-acetate having a melting point of 139°–141° C.

(B) 2.2 g of phenyl 5-tert-butoxycarbonyl-hexahydro-2-methyl-1,3-dioxo-1H-pyrazolo[1,2-a]-pyridazine-2-acetate in 12 ml of 1,2-dimethoxyethane were treated with 9 ml of methanolic hydroxylamine (prepared by dissolving 1.38 g of hydroxylamine hydrochloride in methanol, adding 1.12 g of potassium hydroxide pellets in methanol to a total volume of 14 ml and filtering the solution before use). After 18 hours, the solvent was removed, 300 ml of ethyl acetate were added and the mixture was washed with dilute sodium chloride solution followed by saturated sodium chloride solution. The organic phase was dried over magnesium sulfate and evaporated, there being thus obtained an oil which crystallized from ethyl acetate to give 0.98 g of tert.butyl hexahydro-2-[(N-hydroxycarbamoyl)methyl]-2-methyl-1,3-dioxo-1H-pyrazolo[1,2-a]pyridazine-5-carboxylate having a melting point of 157°–165° C. (decomposition).

(C) 0.8 g of tert.butyl hexahydro-2-[(N-hydroxycarbamoyl)-methyl]-2-methyl-1,3-dioxo-1H-pyrazolo[1,2-a]pyridazine-5-carboxylate was treated with 10 ml of trifluoroacetic acid for 1 hour and the mixture was then evaporated. The residue was treated with 5 ml of ethyl acetate and the mixture was evaporated. Trituration of the residue with 1,2-dimethoxy-ethane and recrystallization from methanol/water yielded 0.21 g of hexahydro-2-[(N-hydroxycarbamoyl)methyl]-2-methyl-1,3-dioxo-1H-pyrazolo[1,2-a]pyridazine-5-carboxylic acid having a melting point of 254° C. (decomposition).

EXAMPLE 20

(A) A solution of 27 g of 1-benzyloxycarbonylpiperazic acid tert.butyl ester in 500 ml of dichloromethane was treated with 250 ml of saturated aqueous sodium bicarbonate, 30 g of sodium bromide in 50 ml of water and 28.6 g of 3-bromo-2-bromomethylpropanoyl chloride. The mixture was stirred at room temperature for 18 hours, the organic layer was separated, dried over magnesium sulfate and evaporated. The residue was chromatographed on 400 g of silica gel using 2 to 5% ethyl acetate in toluene for the elution. There were obtained, after crystallization from ethyl acetate/hexane, 27.3 g (59%) of 1-benzyl 3-tert.butyl 2-(3-bromo-2-bromomethylpropanoyl)-hexahydropyridazine-1,3-dicarboxylate having a melting point of 101°–102° C.

(B) 13.3 g of 1-benzyl 3-tert.butyl 2-(3-bromo-2-bromomethyl-propanoyl)-hexahydropyridazine-1,3-dicarboxylate in 122 ml of acetic acid and 122 ml of methanol was hydrogenated undera pressure of 1 atmosphere for 16 hours in the presence of 1.4 g of 10% palladium/charcoal, the hydrogenation being carried out under a soda-lime trap. The catalyst was removed by filtration, the filtrate was treated with 3.2 g of sodium acetate trihydrate and then evaporated. The residue was extracted with 300 ml of ethyl acetate and the solution was chromatographed on 400 g of silica gel using diethyl ether/hexane for the elution. There were obtained 1.25 g of tert.butyl 2-bromomethyl-hexahydro-3-oxo-1H-pyrazolo[1,2-a]pyridazine-5-carboxylate (diastereomer A) having a melting point of 109°–111° C. (from hexane), 2.45 g of tert.butyl 2-bromomethyl-hexahydro-3-oxo-1H-pyrazolo[1,2-a]-pyridazine-5-carboxylate (diastereomer B) having a melting point of 88°–89° C. (from hexane) and 1.20 g of a mixture of the aforementioned diastereomers.

(C) 1.42 g of tert.butyl 2-bromomethyl-hexahydro-3-oxo-1H-pyrazolo[1,2-a]pyridazine-5-carboxylate (diastereomer A) and 0.58 g of potassium thioacetate were stirred at room temperature in 20 ml of acetone for 17 hours. The solvent was removed by evaporation, the residue was diluted with 100 ml of ethyl acetate, the mixture was washed three times with sodium chloride solution, dried over magnesium sulfate and evaporated. After recrystallization of the residue from ethyl acetate/hexane, there were obtained 1.07 g of tert.-butyl 2-acetylthiomethyl-hexahydro-3-oxo-1H-pyrazolo[1,2-a]-pyridazine-5-carboxylate (diastereomer A) having a melting point of 92°–93° C. (from ethyl acetate/hexane).

EXAMPLE 21

2.3 ml of 1,5-diazabicyclo[5.4.0]undec-5-ene in 10 ml of dioxan were added at 5° C. to a solution of 4.4 g of tert.butyl 2-bromomethyl-hexahydro-3-oxo-1H-pyrazolo[1,2-a]-pyridazine-5-carboxylate (diastereomer B) in 25 ml of dioxan. The mixture was left to stand at room temperature for 2 hours and then filtered. The filtrate was evaporated and the residue was dissolved in ethyl acetate. The solution was filtered through 6 g of silica gel and evaporated. The residue obtained was dissolved in 10 ml of acetone. The solution was treated with 1.6 g of potassium thioacetate and subsequently with 10 ml of thioacetic acid, whereupon the mixture was stirred overnight at room temperature. The mixture was diluted with 100 ml of dichloromethane and washed with 50 ml of saturated aqueous sodium bicarbonate. The separated organic phase was dried over magnesium sulfate and evaporated to give an oil which was chromatographed over 200 g of silica gel using diethyl ether/hexane for the elution. After recrystallization from ethyl acetate/hexane, there were obtained 1.69 g of tert.butyl 2-acetylthiomethyl-hexahydro-3-oxo-1H-pyrazolo[1,2-a]pyridazine-5-carboxylate (diastereomer A) and 0.9 g of the corresponding diastereomer B.

EXAMPLE 22

1.69 of tert.butyl 2-acetylthiomethyl-hexahydro-3-oxo-1H-pyrazolo[1,2-a]pyridazine-5-carboxylate (diastereomer A) were treated with 10 ml of trifluoroacetic acid at room temperature for 2 hours. The solution was evaporated and the residue was re-evaporated with toluene several times. The residue was then crystallized from acetone to give 1.1 g of 2-acetylthiomethyl-hexahydro-3-oxo-1H-pyrazolo[1,2-a]-pyridazine-5-carboxylic acid having a melting point of 166°–168° C. (decomposition).

EXAMPLE 23

1.8 g of 2-acetylthiomethyl-hexahydro-3-oxo-1H-pyrazolo[1,2-a]pyridazine-5-carboxylic acid were heated at 95° C. for 1.5 hours in 2 M hydrochloric acid. The mixture was cooled, the pH was adjusted to 3 by the addition of disodium hydrogen orthophosphate and the aqueous solution was extracted repeatedly with ethyl acetate. The organic extracts were dried over magnesium sulfate and evaporated. After recrystallization of the residue from acetone, there were obtained 1.1 g of hexahydro-2-mercaptomethyl-3-oxo-1H-pyrazolo[1,2-a]pyridazine-5-carboxylic acid having a melting point of 145.5°–147° C.

EXAMPLE 24

(A) A mixture of 6.4 g of 1-benzyloxycarbonylpiperazic acid tert.butyl ester and 2.56 g of 3-methyldihydro-2(3H)-furanon-3-ylcarboxaldehyde (J. Med. Chem. 1976, 19 309–313) in 200 ml of methanol was hydrogenated over 0.9 g of 10% palladium/carbon at room temperature and atmospheric pressure. The catalyst was filtered off. The filtrate was evaporated and the residue was chromatographed over silica gel to give 3.3 g (56%) of 6-tert-butyl-3a-methyl-4-oxo-2,3,4,6,7,8,9,10a-octahydro-furo[2,3-c]pyrazolo[1,2-a]pyridazine-6-carboxylate (diastereomer A) in the form of a yellowish oil.

(B) 1.62 g of 6-tert-butyl-3a-methyl-4-oxo-2,3,4,6,7,8,9,10a-octahydro-furo[2,3c]pyrazolo[1,2-a]pyridazine-6-carboxylate (diastereomer A) were dissolved in 25 ml of water and 10 ml of dioxan, the solution was treated with 2.75 ml of 2 M hydrochloric acid and the mixture was hydrogenated over 160 mg of 10% palladium/carbon at room temperature and under atmospheric pressure. The catalyst was filtered off, the filtrate was evaporated and the residue was evaporated with pyridine. The residue, in 15 ml of pyridine, was treated dropwise at 0° C. with 1.27 ml of methanesulfonyl chloride. The mixture was stirred at 0° C. for 2 hours, the suspension was then evaporated and the residue was partitioned between 50 ml of chloroform and 10 ml of 2 M hydrochloric acid. The organic phase yield, after washing with sodium chloride solution and chromatography on silica gel, 0.77 g (37%) of tert.butyl hexahydro-2-(2-methanesulfonyloxyethyl)-2-methyl-3-oxo-1H-pyrazolo[1,2-a]pyridazine-5-carboxylate (diastereomer A) in the form of an oil.

(C) A solution of 0.77 g tert.butyl hexahydro-2(2-methanesulfonyloxyethyl)-2-methyl-3-oxo-1H-pyrazolo[1,2-a]-pyridazine-5-carboxylate (diastereomer A) in 20 ml of acetone was treated with 0.3 g of sodium iodide and 0.23 g of potassium thioacetate. The mixture was then stirred at room temperature for 24 hours and subsequently evaporated. After chromatography of the residue on silica gel, there was obtained 0.43 g (59%) of tert.butyl hexahydro-2-(2-acetylthioethyl)-2-methyl-3-oxo-1H-pyrazolo[1,2-a]pyridazine-5-carboxylate (diastereomer A) in the form of an oil.

(D) 0.43 g of tert.butyl hexahydro-2-(2-acetylthioethyl)-2-methyl-3-oxo-1H-pyrazolo[1,2-a]pyridazine-5-carboxylate (diastereomer A) in 2 ml of trifluoroacetic acid was left to stand at room temperature for 2 hours. The mixture was evaporated to dryness and the residue was stirred under nitrogen with 6 ml of water/concentrated ammonium hydroxide (50:50) for 2 hours. The mixture was acidified to pH 3 with hydrochloric acid, saturated with sodium chloride and extracted with chloroform. Chromatography of silica gel yielded 0.16 g of an off-white solid. Recrystallization from ethyl acetate/hexane yielded 0.1 g (32%) of hexahydro- 2-(2-mercaptoethyl)-2-methyl-3-oxo-1H-pyrazolo[1,2-a]-pyridazine-5-carboxylic acid (diastereomer A) in the form of off-white crystals having a melting point of 119°–122° C.

The following Examples illustrate pharmaceutical preparations containing the pyrazolopyridazine derivatives of formula I of invention:

EXAMPLE A

Tablets containing the following ingredients are produced in a conventional manner:

| Ingredient | Per tablet |
| --- | --- |
| Pyrazolopyridazine derivative of Formula I | 10.0 mg |
| Lactose | 125.0 mg |
| Maize starch | 75.0 mg |
| Talc | 4.0 mg |
| Magnesium stearate | 1.0 mg |
| Total weight | 215.0 mg |

EXAMPLE B

Capsules containing the following ingredients are produced in a conventional manner:

| Ingredient | Per capsule |
| --- | --- |
| Pyrazolopyridazine derivative of Formula I | 25.0 mg |
| Lactose | 150.0 mg |
| Maize starch | 20.0 mg |
| Talc | 5.0 mg |

| Ingredient | Per capsule |
|---|---|
| -continued | |
| Total weight | 200.0 mg |

We claim:

1. A compound of the formula

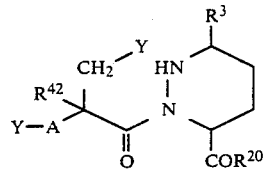

wherein A is methylene, ethylene or propylene which may be substituted by lower alkyl, Y is halogen, $R^3$ is hydrogen, lower alkyl, benzyl, phenyl or phenyl bearing one or more substituents selected from the group consisting of halogen, lower alkyl, lower alkoxy and trifluoromethyl, $R^{20}$ is lower alkoxy and $R^{42}$ is hydrogen, lower alkyl, benzyl, phenyl, phenyl bearing one or more substituents selected from the group consisting of halogen, lower alkyl, lower alkoxy and trifluoromethyl or a group of the formula —A—Y in which A and Y are as described above.

* * * * *